United States Patent [19]

Finney

[11] 4,307,723

[45] Dec. 29, 1981

[54] EXTERNALLY GROOVED URETERAL STENT

[75] Inventor: Roy P. Finney, Tampa, Fla.

[73] Assignee: Medical Engineering Corporation, Racine, Wis.

[21] Appl. No.: 119,865

[22] Filed: Feb. 8, 1980

Related U.S. Application Data

[63] Continuation-in-part of Ser. No. 894,278, Apr. 7, 1978, Pat. No. 4,212,304.

[51] Int. Cl.³ ............................................. A61M 25/00
[52] U.S. Cl. .................................................. 128/349 R
[58] Field of Search .......... 128/349 R, 349 B, 350 R, 128/350 V, 348 R, 419 P

[56] References Cited

U.S. PATENT DOCUMENTS

| | | | |
|---|---|---|---|
| 1,060,665 | 5/1913 | Bell ................................. | 128/349 R |
| 2,043,630 | 6/1936 | Raiche ............................. | 128/349 B |
| 2,118,631 | 5/1938 | Wappler .......................... | 128/349 R |
| 2,221,138 | 11/1940 | Hendrickson ................... | 128/349 R |
| 2,320,157 | 5/1943 | Raiche ............................. | 128/349 B |
| 3,419,010 | 12/1968 | Williamson ..................... | 128/350 |
| 3,630,206 | 12/1971 | Gingold .......................... | 128/349 B |
| 3,890,977 | 6/1975 | Wilson ............................. | 128/349 R |
| 4,033,331 | 7/1977 | Guss et al. ...................... | 128/348 |
| 4,117,836 | 10/1978 | Erickson ......................... | 128/348 |

Primary Examiner—Richard J. Apley
Assistant Examiner—T. Brown
Attorney, Agent, or Firm—Quarles & Brady

[57] ABSTRACT

The stent is an elongated, flexible generally cylindrical member. One of the ends of the stent is closed and set in the form of a hook and the other end is set in the form of a hook with a long intermediate portion connecting the hook ends. The stent is provided with at least one longitudinally extending groove to provide a passage for fluid and a wire stylet. The stylet is used to straighten the curved ends so that the stent can be cystoscopically inserted within the patient, the stylet being removed when the stent is properly positioned so that upon removal the hooks will reform and prevent the stent from migrating.

14 Claims, 8 Drawing Figures

EXTERNALLY GROOVED URETERAL STENT

The present application is a continuation-in-part of my earlier patent application Ser. No. 894,278 filed Apr. 7, 1978 (Pat. No. 4,212,304) entitled "Ureteral Catheter Stent".

The present invention relates to ureteral catheter stents. More particularly, it relates to an externally grooved ureteral stent which can be introduced both cystoscopically or during open surgery and which once in place resists migration and encrustation.

BACKGROUND OF THE INVENTION

Indwelling ureteral catheter stents or drainage tubes have been used to bypass ureteral obstructions or ureterovaginal fistulas and maintain urinary drainage. In the past, stents made of open end silicone tubing have been used for this purpose and have provided good drainage for sustained periods of time. However, the use of such open end tubing has not been completely satisfactory. For example, in some instances, the tubing has migrated and in others it has been expelled. In still other instances, the lumen of the tubing has become encrusted greatly reducing urinary drainage.

Various attempts have been made to produce stents which do not have the problems which accompany the use of open end tubing. For example, stents have been designed which are closed at one end to facilitate passage into a body passage and which have radial passageways in the wall connecting the lumen to the outside and a flange at the other end to make upward migration of the stent less likely. Another approach to prevent migration has been to provide the body of the stent with sharply pointed barbs which are designed to prevent downward migration and explusion. However, such barbs increase the diameter of the stent making it more difficult to insert and in some instances can cause the stent to migrate outside the bladder to create medical or other problems for the urologist. Recently, a stent has been introduced which is made of stiff polyethylene. It has a relatively small flange on the distal end which is intended to prevent upward migration, and the proximal end is formed in the shape of a pigtail. Unfortunately, this stent must be introduced by the relatively complex Seldinger technique. Furthermore, the relatively small flange has not always prevented the stent from passing above the bladder making removal uncertain.

All the prior art stents have one feature in common; they are primarily designed to be passed endoscopically in a retrograde fashion and not during open surgery.

The ideal ureteral stent should have at least the following desirable characteristics: (1) The stent should be made of a material which is soft, quite flexible and resists tissue reaction and encrustation; (2) it should be radiopaque; (3) to facilitate its passage it should be of a uniform diameter throughout without barbs or flanges; (4) it should be easily passed during open surgery as well as endoscopically; (5) it should have means to prevent migration in either direction; and (6) it should be able to withstand repeated sterilization. It also would be desirable if the stent would be of a design which resists plugging of flow due to encrustation.

In my earlier patent application, Ser. No. 844,278, filed Apr. 7, 1978, I disclosed an improved ureteral stent having a hook at each end to prevent migration. This stent has proven to be a significant advance in the art of ureteral stents in that it does not migrate and it resists encrustation extremely well in noninfected urine, especially when the stent is formed of a silicone elastomer. However, even such stents of silicone elastomer can become encrusted with various materials found in urine in the presence of infections.

Certain bacteria which commonly cause urinary tract infections (proteus and pseudomonas) can cause severe encrustation. These organisms produce an enzyme which can break down urea, a normal component of all urine into ammonia. Therefore, they are called "urea splitting" bacteria. Ammonia makes the normally acid urine highly alkaline. As the calcium salts in the urine are much more soluble and are often near saturation in the normal acid urine, these salts, especially calcium phosphate, precipitate out in the alkaline urine caused by the urea splitting organisms. In the face of a urinary tract infection, the stents may have calcium phosphate encrusted within, which completely obstructs the lumen of the stent thus interfering with urinary drainage.

SUMMARY OF THE INVENTION

It is the general object of the present invention to disclose a ureteral catheter stent which is easily introduced both cystoscopically and during open surgery, and which once in place both resists migration and resists plugging due to encrustation.

It is a still further object to disclose a stent which has at least one longitudinal groove on its external surface through which fluid can drain.

I have now discovered that a ureteral stent which has at least one external longitudinal extending groove to promote urine drainage around the stent will resist plugging due to encrustation and maintain flow even in the presence of urinary infection. The reason that the external groove does not become encrusted is that the ureter transports urine in an active fashion from the kidney to the bladder by peristalsis. Successive constrictive rings of peristaltic movement propel successive boluses of urine to the bladder. The peristaltic contraction rings moving down over the outer surface of the stent when it is in place keep the outer surface of the stent, including the external groove, swept clean of encrustation. The first microscopic crystals whih tend to form are swept off by the peristaltic movement.

In a preferred embodiment, the stent comprises an elongated flexible cylindrical member of substantially uniform outside diameter throughout its length which has proximal and distal ends which are set in the form of hooks. There is at least one external longitudinally extending groove which provides a passage for fluid along the outside of the member. The stent has an internal lumen which is large enough to allow the passage of a small wire stylet for the purpose of straightening the hooks so that the stent can be inserted cystoscopically. To pass the grooved stent in open surgery, it also is advisable to have several small radial passages through the side wall that permit the wire stylet to be inserted through the radial passage into the lumen to straighten one hook so that the stent can be passed in one direction; the other hook can be straightened and passed in the other direction in the same manner.

The groove itself can serve as the indicating means to show which direction the proximal hook will take when the stylet is removed. However, it may be desired where more than one groove is employed to have a separate indicating means such as an index strip. The preferred stent will also have measurement markings every five centimeters along the straight intermediate section.

The two gently formed opposed hooks of the stent prevent it from migrating either upwardly or downwardly once it is in place. Means for increasing the rigidity of the proximal and distal hooks may be incorporated. Plastic, fabric, metal, or other suitable material, may be incorporated into the hooks to make them less flexible and therefore make them more resistant to migration. The hooks extend in opposite directions so that when used as an indwelling ureteral stent the proximal end can hook into the lower calix or renal pelvis while the distal end curves out into the bladder. This design also prevents the tip of the stent from impinging directly into the bladder mucosa thereby decreasing discomfort and inflammation.

These and still other objects and advantages of the invention will be apparent from the description which follows.

DESCRIPTION OF THE PREFERRED EMBODIMENT

Figure 1:
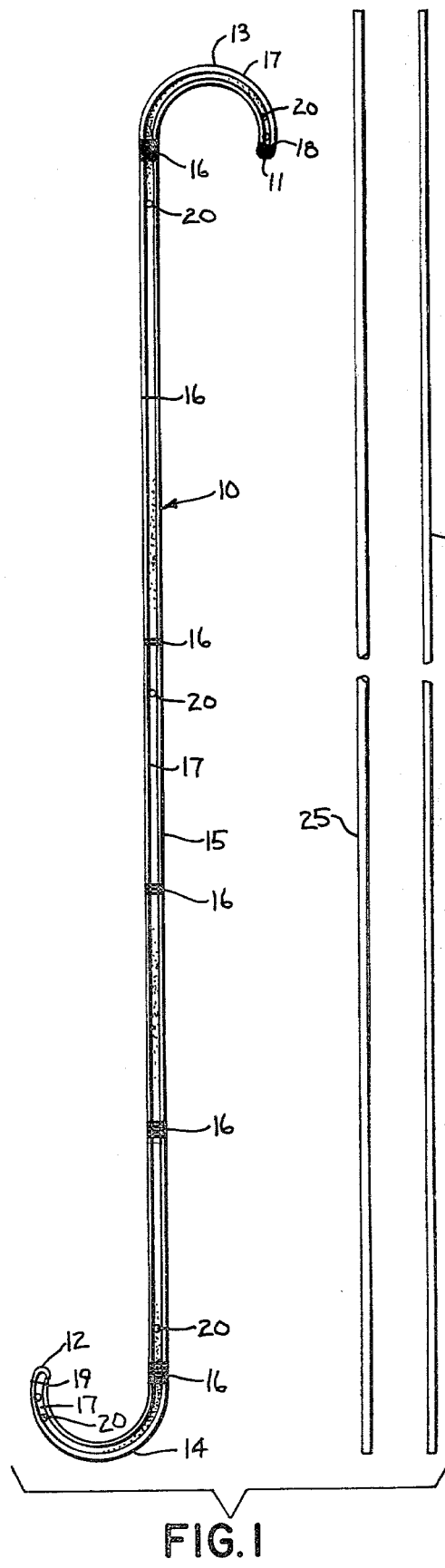
FIG. 1 is a perspective view of the preferred stent of the present invention and means for inserting the stent.

In the preferred embodiment shown in FIGS. 1 to 4, the stent 10 is seen to be an elongated tubular member which is closed at both ends 11 and 12. Portions adjacent each end are formed and set in the shape of gently curved hooks 13 and 14 which extend in opposite directions. A relatively straight intermediate section 15 extends between the opposed hooks 13 and 14. The section 15 is provided with measurement markings 16, which are preferably spaced 5 centimeters apart. The stent 10 is supplied in 7 French and 8.5 French O.D. sizes in 16, 24, 26, 28 and 30 cm lengths. The listed length of the stent 10 is the length of the section 15 and does not include the hooked ends 13 and 14. This allows the user to radiographically estimate the ureteral length and select the proper stent for passage.

Figure 2:
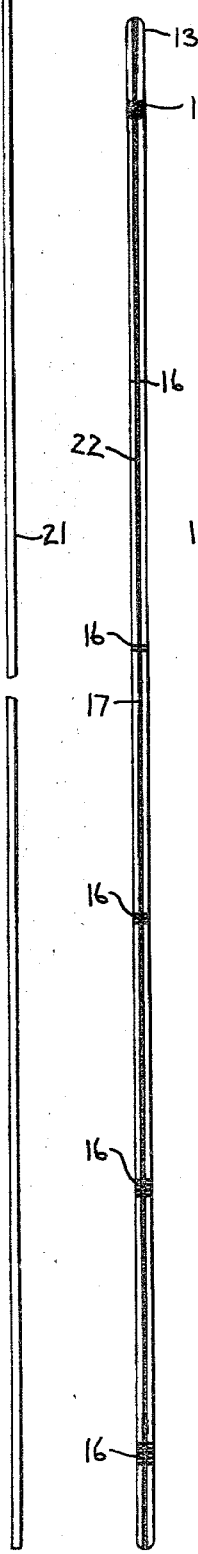
FIG. 2 is a back elevational view of the stent of FIG. 1.
Figure 4:
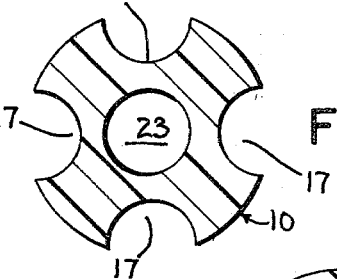
FIG. 4 is a sectional view taken along lines 4—4 of FIG. 3.

Referring now to FIGS. 1 and 2, it can be seen that there are four longitudinal grooves 17 in the external surface of the stent 10 (as best seen in FIG. 4). The grooves 17 extent substantially the entire length of the stent 10 from a point 18 adjacent the proximal end 11 to a point 19 adjacent the distal end 12. Wire stylet openings 20 are located adjacent each of the hooks 13 and 14 and intermediate the length of the stent 10. The grooves 17 also can serve as indicating means which can be seen through the optics of the cystoscope so that the user can see the direction that the proximal hook 13 and distal hook 14 will form when the straightening metal stylet 21 is removed from the stent 10. If desired, other indicating means can be included such as an index stripe 22 in one of the grooves 17.

Figure 3:
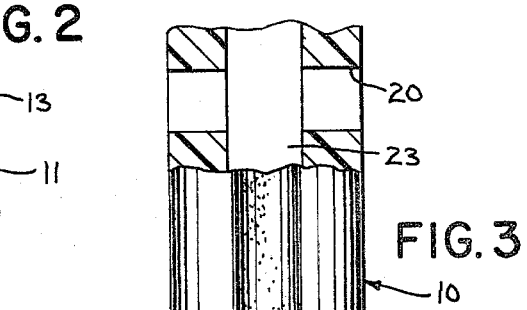
FIG. 3 is an enlarged view of a section of the stent of FIG. 1.

As seen in FIGS. 3 and 4, the stent 10 has a wire stylet receiving lumen 23. The lumen 23 extends from one end 11 of the stent 10 to the other end 12 and is used with the wire stylet 21 to straighten the stent 10 for insertion.

Figure 5A:
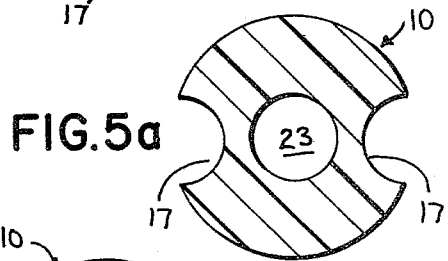
FIGS. 5a to 5d are views similar to FIG. 3 of alternative designs of externally grooved stents.
Figure 5B:
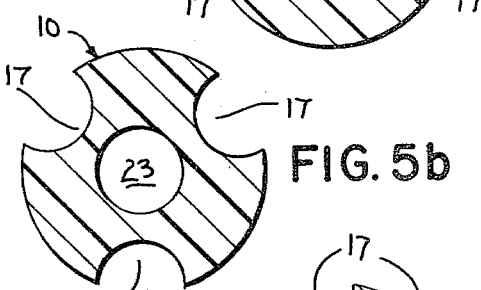
Figure 5C:
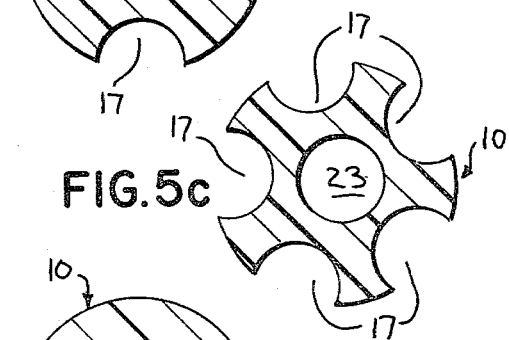

In FIGS. 5a to 5c can be seen the cross sectional shapes of alternative embodiments of the stent having 2, 3 and 5 external grooves, respectively. Embodiments of other shapes can, of course, also be used, if desired.

Figure 5D:
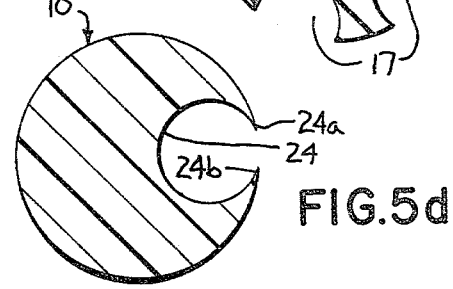

Referring to FIG 5d, there can be seen the cross-sectional shape of an embodiment that does not have a central wire stylet receiving lumen. Instead, groove 24 is provided with lips 24a, 24b which will retain a wire stylet press fit into the groove. A stent having the cross-sectional shape shown in FIG. 5d may also be provided with a stylet tip receiving pocket (not shown) at the proximal end to help retain the stylet in place.

Returning to FIG. 1, there also can be seen a stent pusher 25 and the wire stylet 21 which may be used to help position the stent 10 in a body passage.

The preferred stent 10 is supplied with both ends 11 and 12 closed. As seen in FIG. 1, the proximal end 11 is preferably closed with a colored or opaque material and the distal end 12 with a clear material. When used for endoscopic or cystoscopic insertion, the distal end 12 is clipped and the wire stylet 21 is introduced into the lumen 23 of the stent 10 and passed through substantially the full length of the stent 10 to straighten both hooks 13 and 14.

The stent pusher 25 will normally be supplied as a component of a ureteral catheter stent kit. However, a satisfactory stent pusher 25 may be made from a half length of a standard 5 F ureteral catheter.

In use, the stent pusher 25 is threaded over the wire stylet 21 and inserted 102 mm into the open end of the stent 10. This allows the partial withdrawal and redirection of the stent, if necessary, during standard retrograde catheterization. If necessary, the obstructed ureter is dilated with a standard catheter before inserting the stent 10. Once the stent 10 is properly positioned, the stylet 21 and stent pusher 25 are removed by withdrawing the stent pusher 25 while holding the wire stylet 21 causing the stent 10 and stent pusher 25 to disengage after which the wire stylet 21 and then the stent pusher 25 are withdrawn.

As the stent is of a substantially uniform diameter with both ends smoothly closed and without flanges or barbs or other protrusions, it also may be passed easily during open surgery through a pyelotomy, ureterotomy or transvesically as indicated. When the stent 10 is thus used, the distal end 12 is not clipped. Instead, the stylet 21 is inserted through an opening 20 into the lumen 23 and used to straighten an appropriate length of the stent 10 and a hook 13 or 14. The stent 10 is then easily passed. Once the stylet 21 is withdrawn, the hook once again forms to prevent migration. This same techinque is used to pass the stent 10 into the opposite viscus.

When it is desired to remove the stent 10, it may be removed endoscopically on an outpatient basis using either a foreign body or biopsy forceps or by using a stylet wire with a small hook formed at its end. In any case, once the stent is engaged, it is best removed by withdrawing the entire cystoscope.

The ureteral catheter stent 10 of the present invention is preferably made of silicone elastomer, preferably of the addition-reaction type, which when cured has a durometer of about 70 Shore 'A'. A suitable material is Dow Corning Silicone No. 4772 to which 10% barium sulfate has been added as a radiopaque material. Other plastic materials which resist encrustation with urine salts can also be used.

The stent is preferably formed by extruding uncured tubing of the desired size and cross-sectional shape of a suitable silicone elastomer having the desired durometer. A suitable length of the tubing is then placed in a form to retain the end portions in the shape of gently curved hooks. The thus formed tubing is then cured by heating and the ends closed with silicone. The measurement markings 16 and an index strip 22 may be painted on or otherwise applied and, if desired, then covered with silicone to lock them in place. The openings 20 may be formed by piercing the wall of the tubing with a flattened, sharpened hole cutter of the desired size or by use of a laser or any other conventional means.

The ureteral catheter stent may be supplied in a kit which contains one or an assortment of stents of different sizes and types and which also includes a wire stylet and a stent pusher. In addition, if desired, an open end stent could be included for endoscopic use eliminating the need for the user to clip the distal end.

In the preferred embodiment described and shown in the drawing, the proximal and distal end portions of the catheter stent are both in the form of a gently curved hook. However, it is to be understood that the term "hook" is intended to include other functionally equivalent shapes which prevent migration and do not increase the effective outer diameter of the stent, or complicate its method of introduction. It is also to be understood that externally grooved stents with other means of retention, such as the conventional barbs and flanges in place of the hooks, may be employed with advantage where migration is not a problem and that the shape of the grooves is not critical provided they permit adequate drainage.

It will be readily apparent to those skilled in the art that a number of modifications and changes can be made without departing from the spirit of the invention. For example, if desired, the stent could be equipped at the distal end with a reflux valve such as a flapper valve or the like. Obviously, the stent, although described as ureteral stent, also can be used in other applications than those described in the specification. Therefore, it is to be understood that the scope of the invention is not to be measured by the description, but only the claims that follow.

I claim:

1. A ureteral stent for use in maintaining urinary drainage in a patient, which stent comprises an elongated, flexible, generally cylindrical member of substantially uniform outside diameter throughout its entire length, said member having a proximal end which is closed and set in the form of a hook, a relatively long straight intermediate section and a distal end which is also set in the form of a hook, said member having at least one longitudinally extending external groove to provide a passage for fluid and wire stylet retaining means which permit the use of a wire stylet to straighten the member, including the hooks, so that the member can be cystoscopically inserted and positioned within the patient and which permit the stylet to be removed when the stent is properly positioned so that upon removal the hooks will reform and prevent the member from migrating.

2. A ureteral stent comprises an elongated relatively flexible member having at least one longitudinally extending external groove to provide a passage for fluid flow along the outer surface of the member, the end portions of said member being set in the form of hooks, at least one of which has a rounded end, said member including wire stylet retaining means which enable the user to forcibly straighten the hooks to facilitate the placement of the stent in a body passageway.

3. The stent of claim 2 in which the member is of substantially uniform outer diameter throughout its length.

4. The stent of claim 2 in which the member is of a silicone elastomer material.

5. The stent of claim 2 in which both end portions have rounded ends.

6. The stent of claim 2 in which the member is of an unreinforced silicone elastomer having a durometer of about 70 Shore 'A'.

7. The stent of claim 2 in which the hook portions extend in opposite directions.

8. The stent of claim 2 in which the wire stylet retaining means is a pair of lips on the groove which once the stylet is in the groove prevents the stylet from being accidentally dislodged therefrom.

9. The stent of claim 2 in which the wire stylet retaining means is a longitudinal extending lumen in the member.

10. A kit for providing urinary drainage comprising:
(a) a wire stylet, and
(b) a ureteral catheter stent comprising an elongated relatively flexible member having at least one longitudinally extending external groove to provide a passage for fluid flow, said member having end portions set in the form of hooks at least one of which has a rounded end, and wire stylet retaining means which enable the user to forcibly straighten the hooks to facilitate the placement of the stent in a body passageway.

11. The kit of claim 9 in which the stent is comprised of silicone elastomer having a durometer of about 70.

12. The kit of claim 9 in which both hook portions of the stent have rounded ends.

13. The kit of claim 9 in which the hook portions of the stent extend in opposite directions.

14. The kit of claim 9 in which the stent is of a material which is radiopaque to x-rays.

* * * * *